United States Patent

Wade et al.

[11] 4,092,421
[45] May 30, 1978

[54] METHOD OF CONTROLLING MANURE-BREEDING INSECTS

[75] Inventors: Lisby Lucius Wade; Muriel McDermott, both of Lake Jackson, Tex.

[73] Assignee: The Dow Chemical Company, Midland, Mich.

[21] Appl. No.: 796,648

[22] Filed: May 13, 1977

[51] Int. Cl.² .............................................. A01N 9/22
[52] U.S. Cl. .............................. 424/266; 260/295 AM; 260/295.5 A
[58] Field of Search .................... 424/266; 260/295 E, 260/295 AM, 295.5 A

[56] References Cited

U.S. PATENT DOCUMENTS 3,989,842  11/1976  Wellinga et al. ..................... 424/322

Primary Examiner—Allen J. Robinson
Attorney, Agent, or Firm—Daniel L. DeJoseph; C. Kenneth Bjork

[57] ABSTRACT

A method of controlling manure-breeding insects which comprises orally administering to a warm-blooded animal an insecticidally-effective amount of a compound of the formula

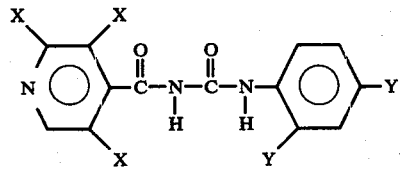

or of the formula

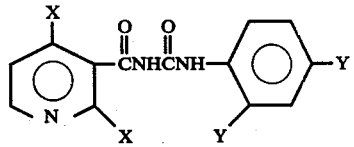

wherein, in both formulas, each X substituent is individually chosen from the group consisting of chlorine and hydrogen; and each Y substituent is individually chosen from the group consisting of chlorine, bromine and hydrogen.

7 Claims, No Drawings

METHOD OF CONTROLLING MANURE-BREEDING INSECTS

BACKGROUND OF THE INVENTION

This invention is concerned with animal husbandry and in particular, is concerned with the control of manure-breeding insects, which are known to be vectors in the transmission of various animal diseases.

One advantage of the method of the present invention is that the compounds utilized therein retain their insecticidal properties after passing through the digestive system of the treated animals. Thus, the application of the insecticidal compounds can be centralized and the number of applications of these compounds can be reduced. This is a distinct advantage when there are a large number of animals to be treated. The method of the present invention is further advantageous in that the insecticides, when used in "feed thru" applications, will be localized directly in the animal's manure where they will be most effective in the control of manure-breeding insects.

DESCRIPTION OF THE INVENTION

These and other advantages as will become apparent from the following specification and appended claims were achieved, according to the present invention's method of controlling manure-breeding insects, by orally administering to a warm-blooded animal an insecticidally-effective amount of a compound of the formula

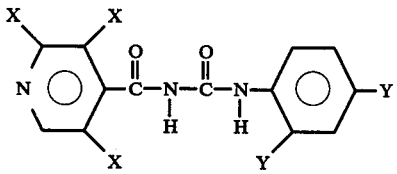

or of the formula

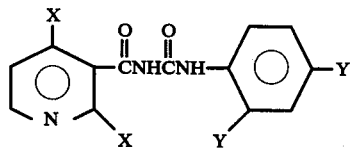

wherein, in both formulas, each X substituent is individually chosen from the group consisting of chlorine and hydrogen; and each Y substituent is individually chosen from the group consisting of chlorine, bromine and hydrogen.

Compounds in accordance with the above formula are alternatively referred to herein as "active compounds".

Examples of active compounds in accordance with the above formula which are utilized in the method of the present invention are:

3,5-Dichloro-N-(((4-chlorophenyl)amino)carbonyl)-4-pyridinecarboxamide (hereinafter referred to as Compound 1);

2,3,5-Trichloro-N-(((4-chlorophenyl)amino)carbonyl)-4-pyridinecarboxamide (Compound 2);

3,5-Dichloro-N-(((phenyl)amino)carbonyl)-4-pyridinecarboxamide (Compound 3);

3,5-Dichloro-N-(((4-bromophenyl)amino)carbonyl)-4-pyridinecarboxamide (Compound 4);

3,5-Dichloro-N-(((2-chlorophenyl)amino)carbonyl)-4-pyridinecarboxamide (Compound 5); and 2,4-Dichloro-N-(((4-chlorophenyl)amino)carbonyl)-3-pyridinecarboxamide (Compound 6).

The active compounds which are utilized in the method of the present invention are highly effective in controlling manure-breeding insects such as houseflies and hornflies. These compounds may be administered to the warm-blooded animals in admixture with their feed or drinking water. Furthermore, the active compounds utilized in the present invention may be administered in the form of tablets, pills, capsules or the like. These active compounds may be admixed with pharmaceutically-acceptable carriers for use in animals; however, they are usually used as a component in the animal feed or drinking water.

The insecticidally-effective dosage desirable for effective use of preparations containing active compounds will naturally depend on various factors such as the active compound or compounds chosen and the form of preparation. Moreover, the activities of the compounds against different insects will vary from compound to compound. It is only necessary that one or a combination of the compounds be orally administered in a sufficient amount so as to make possible the application of an insecticidally-effective or inactivating dosage. Generally, one or a combination of the active compounds can be orally administered to a warm-blooded animal, especially a ruminant, at a daily dosage of from about 0.25 to about 1.0 milligram of active compound per kilogram of animal body weight.

When administered to poultry, an effective dosage rate will generally range from about 5 parts to about 50 parts of active compound per million parts of poultry feed.

These compounds may be effectively administered to warm-blooded animals especially ruminants, dogs, horses, swine and poultry.

EXAMPLES

The examples which follow should not be construed as limitations upon the overall scope of the invention.

EXAMPLE 1

A calf weighing 234.5 kilograms was, for five days, administered Compound 1 daily in its feed at a dose rate of 0.5 milligrams per kilogram of body weight. Thus, the calf was fed 117 milligrams of the compound every day. On the fourth, fifth and sixth day of the test, quart size manure samples were collected from the treated animal and frozen to kill any wild insect larvae that may have been present. The samples were thawed and were seeded with equal amounts of eggs from colony strains of hornflies and houseflies. Control samples were also similarly seeded at that time. The samples were incubated at 80° F for a period of time sufficient to allow the eggs to hatch.

The percent control was determined by counting the number of normal adult flies that hatched from the treated samples and comparing this figure with the number of flies that hatched from the untreated (control) samples. It was determined that there was, in the treated samples, 100% control of hornflies and 97% control of houseflies. The above compound was similarly tested at a dose rate of 0.25 milligrams per kilogram of body weight and exhibited 100% control of hornflies and 76% control of houseflies.

EXAMPLE 2

Using the procedure of Example 1, Compounds 2, 3, 4, 5 and 6 were likewise tested for housefly and hornfly control at various dose rates. The results of these tests are set forth in Table 1.

TABLE 1

| Compound | DOSE RATE (Milligrams per Kilogram of Animal Body Weight) | Percent Control of Hornflies | Percent Control of Houseflies |
|---|---|---|---|
| 2 | 1 | 100 | — |
| 3 | .5 | 100 | 97 |
| 4 | .2 | 99 | 87 |
| 5 | .1 | 97 | 65 |
| 6 | .6 | 99 | — |

EXAMPLE 3

Compound 1 was added to chicken feed at the rate of 5 parts of compound per million parts of feed. Samples of chicken droppings were collected and, after being frozen and thawed, were seeded with larvae from DDT-resistant and DDT-susceptible strains of houseflies. Control samples were also seeded. The tests were repeated 3 parts of compound per million parts of feed. Table 2 sets forth the percent control of the susceptible and resistant strains at the indicated concentrations.

TABLE 2

| Percent Control of Housefly Larvae Using Compound 1 | | |
|---|---|---|
| | Parts of Compound 1 Per Million Parts Feed | |
| Strain | 5 | 3 |
| Resistant | 0 | 0 |
| Susceptible | 50 | 80 |

PREPARATION OF THE ACTIVE COMPOUNDS

The active compounds utilized in the present invention's method can be prepared by reacting an appropriately substituted pyridine carboxamide with an appropriately substituted phenyl isocyanate in the presence of an organic solvent.

The reaction is carried out by contacting the reactants together in equimolar proportions in the presence of a solvent at a reaction temperature which, at atmospheric pressure, may vary from 0° C to the boiling point of the solvent used. Examples of suitable solvents are aromatic hydrocarbons such as benzene or xylene, chlorinated hydrocarbons such as chloroform, methylene chloride or ethylene chloride or other inert solvents such as acetonitrile.

Following the completion of the reaction (generally lasting from 0.5 to 24 hours), the mixture is cooled and the precipitated product is collected by filtration or other suitable techniques. This precipitated product usually is washed with a solvent such as xylene and dried. The resulting product may be further purified, if desired, by recrystallization from a solvent such as, for example, aqueous acetic acid, or by other purification procedures.

What is claimed is:

1. A method of controlling manure-breeding insects which comprises orally administering to a warm-blooded animal an insecticidally-effective amount of a compound of the formula

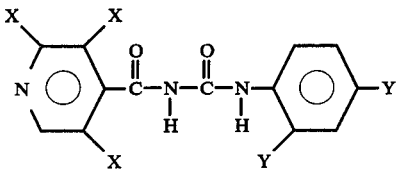

or of the formula

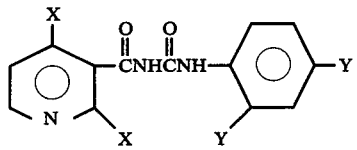

wherein, in both formulas, each X substituent is individually selected from the group consisting of chlorine and hydrogen; and each Y substituent is individually chosen from the group consisting of chlorine, bromine and hydrogen.

2. The method of claim 1 wherein the compound is 3,5-Dichloro-N-(((4-chlorophenyl)amino)carbonyl)-4-pyridinecarboxamide.

3. The method of claim 1 wherein the compound is 2,3,5-Trichloro-N-(((4-chlorophenyl)amino)carbonyl)-4-pyridinecarboxamide.

4. The method of claim 1 wherein the compound is 3,5-Chloro-N-(((phenyl)amino)carbonyl)-4-pyridinecarboxamide.

5. The method of claim 1 wherein the compound is 3,5-Dichloro-N-(((4-bromophenyl)amino)carbonyl)-4-pyridinecarboxamide.

6. The method of claim 1 wherein the compound is 3,5-Dichloro-N-(((2-chlorophenyl)amino)carbonyl)-4-pyridinecarboxamide.

7. The method of claim 1 wherein the compound is 2,4-Dichloro-N-(((4-chlorophenyl)amino)carbonyl)-3-pyridinecarboxamide.

* * * * *